United States Patent [19]

Merkl

[11] 3,957,598

[45] *May 18, 1976

[54] METAL HYDRATES AND SALTS OF CARBOXYLIC ACIDS

[76] Inventor: George G. Merkl, 46 Sunset Court, Haworth, N.J. 07641

[ * ] Notice: The portion of the term of this patent subsequent to Dec. 24, 1991, has been disclaimed.

[22] Filed: May 13, 1974

[21] Appl. No.: 469,125

Related U.S. Application Data

[63] Continuation of Ser. No. 255,758, May 22, 1972, abandoned.

[52] U.S. Cl. .............................. 204/72; 204/59 R; 260/429.9; 260/430; 260/436; 260/438.1; 260/439 R; 260/448 A
[51] Int. Cl.² ...................... C25B 3/00; C07F 7/24; C07F 3/06; C07F 5/06
[58] Field of Search ............. 204/59 R, 59 QM, 72; 136/86 A, 154; 260/448 R, 429.9, 436 R, 438.1, 430

[56] References Cited
UNITED STATES PATENTS

| 535,464 | 3/1895 | Schaeffer | 136/154 |
|---|---|---|---|
| 1,427,011 | 8/1922 | Orsolino | 136/154 |
| 1,863,254 | 6/1932 | Polin | 75/169 |
| 2,042,019 | 5/1936 | Pasternack et al. | 260/448 R |
| 2,275,211 | 3/1942 | Urbain et al. | 260/448 R |
| 3,574,607 | 4/1971 | Merkl | 75/134 |
| 3,578,439 | 5/1971 | Merriman | 75/169 |
| 3,856,841 | 12/1974 | Merkl | 260/448 A |

*Primary Examiner*—F. C. Edmundson
*Attorney, Agent, or Firm*—Arnold, White & Durkee

[57] ABSTRACT

A metal salt of a carboxylic acid is formed by contacting a carboxylic acid with an activated metal. The activated metal is formed by combining a first metal with a second metal which has an affinity for hydrogen in the presence of a proton source. Typically, an activated aluminum is formed from a highly pure aluminum rod combined with an alloy of indium and gallium in the presence of hydrochloric acid. The addition of excess water in the presence of the carboxylic acid and activated metals forms a polymeric metal salt from a water soluble carboxylic acid.

9 Claims, 5 Drawing Figures

ALUMINUM OXALATE

METAL HYDRATES AND SALTS OF CARBOXYLIC ACIDS

This is a continuation of application Ser. No. 255,758, filed May 22, 1972, now abandoned.

CROSS REFERENCE

Copending application, "Catalytic Electrode", Ser. No. 211,979, filed Dec. 27, 1971, now abandoned provides numerous examples for the preparation of diverse activated metals. Reference is had to the copending application, Ser. No. 469,126, filed May 13, 1974.

PRIOR ART

The present invention relates to the method of forming metal salts of carboxylic acids and to a new class of polymeric metal salts of carboxylic acids.

Generally a metal salt of a carboxylic acid is a compound formed by a metal substituted for a hydrogen ion and is termed a metallic soap or simply a soap. The literature indicates that metallic soaps divide sharply into two classes, the first being quite water soluble and consisting of compounds based on the alkali metals, with the exception of some lithium derivatives. The second group consists of substantially water insoluble and hydrocarbon soluble compounds, and includes metal salts of both the alkaline earths and heavy metals. It is the latter group which is generally indicated, when metallic soaps are mentioned.

The prior art teaches that to form the metallic soaps the anion cannot be too small and seven carbon atoms is often taken as a preferred minimum preferred. The most common method of preparing the metallic soaps is by fusion. An oxide or hydroxide is fused into an acid at an elevated temperature to complete the reation and remove the water. Another commonly employed method is to react a water solution of the sodium salt of an acid with a solution of an appropriate metal salt, such as the chloride. In this instance, the impurities are washed away and the pulp dehydrated at an elevated temperature.

Metallic soaps find wide applications in industry. One common use of these soaps is as a drier in paints, varnishes and ink. Although the metallic soaps are really oxidation and polymerization catalysts, the term "drier" was used early in the paint field and is still used to refer to the soaps. The term is derived from the apparent drying of unsaturated oils in which the catalyst has been included, the liquid gradually changing to the solid state commonly desired in protective and decorative coatings.

The drier, in practice, must be incorporated into vehicles (paints, varnishes, printing ink, etc.) which chemically have a polyfunctional structure. Polyenes, as exemplified by the drying oils such as linseed oil, represent a common example of compounds in which two or more intermolecular linkages may be established. When these linkages are present, three dimensional growth becomes possible and gelable drying type compounds may be produced.

The solidification of a film is extremely complex but it is thought to involve oxidation polymerization and association. Oxidation usually occurs first, peroxide intermediates then form and initiate chain polymerization, as well as carbonoxygen-carbon linkages and hydroxylated derivatives. Polymerization also progresses, a copious supply of free radicals being available from the oxidation process. Finally, because of the large, and frequently polar molecules which form as a result of the two aforementioned steps, association of molecules through van der Waal forces, hydrogen bonding, and other mechanisms occurs.

An obvious effect of the drier is to shorten the time before oxygen combines with the film in a measurable amount, i.e., the induction period. Once the induction period has been passed, oxygen combines with the material at a much greater rate when an oxidation catalyst is present. It is generally thought that metals having a multiple valence state act as good catalysts and are preferred.

It is known that a lead soap is an effective catalyst which causes solidification of the film at an earlier state in the oxidation process, presumably because polymerization is progressing concurrently. Secondly, there is a decrease in the total oxygen combined with the oil when it has solidified in the presence of driers. Further polymerization of the film usually is more advanced at the gel point in the latter case.

Even though metallic soaps constitute a large and useful family of compounds, investigations have been limited because of the great complexities encountered by prior art methods. Many of the metallic soaps whose formulas may be predicted from simple valence rusles can often be prepared only as hydrates or basic salts or mixtures of the two.

Metallic soaps find applications such as for glass destruction, that is, flattening paints, thickening greases and as waterproofing agents.

Water soluble soaps form a large class of compounds, many of which have been prepared as pure compounds. When anhyrous, they are microcrystalline solids, which upon heating, undergo several phase changes into liquid crystalline phases and finally melt to isotropic liquids at temperatures in the order of 300°C.

Water soluble soap solutions are commonly used as detergents. The detergent properties of the aqueous soap solution is attributed to the structure of the soap. Typically, the soap has a small hydrophilic cation and larger anion which is heterpolar having a hydrophilic $COO^-$ group and a long hydrophibic hydrocarbon chain. At all concentrations, the hydrophobic chain tends to concentrate at the surface of the solution and thereby reduce the surface tension. A greater reduction in surface tension appears to result for metal salts having a large hydrocarbon group. Since prior art methods have resulted in metal salts of carboxylic acids having carbon chains higher than eight being insoluble in water, it has been a practice to use salts of sulphonic acids, since their long chain metal salts are soluble in water. The tendency for a soap solution to orientate the hydrocarbons at the surface also brings about ease in foaming and a very high stability of films of the soap solution.

The prior art shows the existence of what has been called basic metal salts. These can be analogized to the polymeric metal salts as used in the present specification. A basic salt is characterized by the presence of a stoichiometric excess in metal relative to the equivalent number organic acid groups present therein based on the normal stoichiometry of the particular metal and organic acid. For example, if a normal magnesium salt has a ratio of magnesium to the acid of 1:1, the basic salt would have a higher ratio, e.g. 1.1:1, 2:1, 5:1, etc. According to prior art not all organic acids are susceptible to the formation of basic salts. The recognized class of organic acids for this purpose are described in U.S. Pat. No. 3,629,109, 3,312,618, 2,695,910, and 2,616,904. This class is extended by the present invention. Basic salts have also been referred to as being complex salts, superbase salts, and overbase salts. The term "polymeric salts" has been used in German Auslegeschrift No. 1,243,915 since it was realized that the metal salt must be "sticking together" as a polymer in order to accommodate the extra metal atoms.

Prior art methods for preparing basic metal salts have included metal alkoxides and in some cases promoters such as alcohol or oil. The products of the prior art methods have been highly impure and usually mixtures which have included foreign metal oxides and or hydroxides in the resultant product along with an oil in many cases. The expression "overbasing" is probably due to the strongly basic solution which is the product in solution.

In further consideration of the prior art, it is of interest to mention some known organometallic compounds in order to contrast the respective formulas and certain physical properties to the same compounds prepared by the present method. The differences, it is believed, arise due to the high purity of the compounds prepared by the method of the present invention.

Aluminum acetate has been prepared in three forms: $Al(OH)_2(C_2H_3O_2)$, $Al(OH)(C_2H_3O_2)$, and $Al(C_2H_3O_2)_3$. The monoacetate and triacetate are soluble in cold water, whereas the diacetate is only soluble in cold water upon being freshly prepared, otherwise it is a white water insoluble powder. When the diacetate is heated, it loses acetic acid and aluminum-to-oxygen bonding occurs to form an insoluble compound of disputed nature. This latter transformation from solid to solid without melting is important for textile applications.

Aluminum diformate, $Al(OH)(CHO_2)_2 \cdot H_2O$ and aluminum triformate, $Al(CHO_2)_3 \cdot 3H_2O$ are known. Both formates are white powders and, although soluble in water, are used in waterproofing along with other applications.

Aluminum palmitate, $Al(OH)_2(C_{16}H_{31}O_2)$ is a white to yellow powder which is insoluble in water and alcohol.

Aluminum oleate, $Al(C_{18}H_{33}O_2)_3$, is a yellowish mass practically insoluble in water but soluble in alcohol.

Aluminum oxalate, $Al(C_2HO_2)_3 \cdot 4H_2O$ is a white powder practically insoluble in water but soluble in mineral acids.

Aluminum lactate, $Al(C_3H_5O_3)_3$ is a yellowish white powder very soluble in cold water.

Aluminum benzoate, $Al(C_7H_5O_2)_3$ is a white powder only slightly soluble in water.

Aluminum stearate has three known forms: $Al(OH)2(C_{18}H_{35}O_2)$, $Al(OH)(C_{18}H_{35}O_2)_2$ and $Al(C_{18}H_{35}O_2)_3$. Each of the stearates is a white powder which is insoluble in water.

UTILITY

The present invention contrasts prior art methods and compounds in many ways. The present methods are surprisingly simple and economical and yet provide a product of very high purity. Perhaps a most striking feature of the method of the present invention is that any of the ordinary metal salts of a water soluble carboxylic acid can be prepared by merely combining the constituents in accordance with the stoichiometry of the formula of the desired metal salt. The desired metal salt can even be a metal salt based on valence rules alone and not even known to exist beforehand.

According to prior art, no definitive preparation of a pure aluminum tri-soap has been made. Aluminum tri-soaps of water soluble and water insoluble carboxylic acids can be made with the present methods. Surprisingly, the powder form of the metal salts resulting from simply permitting the evaporation of liquid is very fine, with particle sizes in a range of 15–50A. The small particle size is highly advantageous for many applications and prior art methods for preparing metal salts have required additional steps to produce fine particle sizes which have greatly exceeded the particle size that results by the present methods. One application for a fine particle size metal salt is in the paint industry for forming a flat paint.

Furthermore, it is even possible to use the present methods to prepare polymeric metal salts corresponding generally to known formulas or in forms not contemplated to have existed. In addition, the polymeric metal salts prepared by the present invention have a very high purity. These polymeric metal salts have unique properties, such as a water solubility, even for high hydrocarbon groups. Water solutions of these compounds show superior foaming, probably due to the hydrophobic chain-reducing surface tension. The excellent foaming and wetting properties are characteristic of detergents for which these compounds have use.

The polymeric metal salts are also exemplified by the absence of melting points, since heat affects the breaking of internal bonds of the compound subjected thereto to eventually leave a heat stable compound having oxygen bonding of unknown form. The carboxylic radial is thought to be completely lost through the heat transformation.

Another unusual property of the polymeric metal salts is that they have a pH in the range of about 4–5 which is close to the pH of human skin, usually about $4.1 - 4.2p^H$. This property is important for applications involving human contact. For example, a metal salt of myristic acid can be used in a cosmetic base. The prior art basic salts have been alkaline, usually strongly alkaline.

Water insoluble carboxylic acids appear to permit the formation of polymeric metal salts as a mixture although many of the metal salts can be formed with great purity.

The general utility of metal salts of carboxylic acids is well established in the prior art. Among these applications is fireproofing and waterproofing. The polymeric metal salts are outstanding for these applications. In fact, merely dipping a material of a synthetic fiber i.e. polyester, in a polymeric metal salt, say of acrylic acid, imparts fireproofing.

THE ACTIVATED METAL

The present invention relates to methods of forming a metal salt of a carboxylic acid by contacting an activated metal with the carboxylic acid.

Methods of preparing activated metal are amply described in the aforementioned co-pending application but will be succinctly reported herein.

An activated metal is formed by diffusing a second metal into a highly pure first metal in the presence of a proton source. The second metal may be widely selected from such metals as cesium, indium, cadmium, sodium, gallium, and mercury. The second metal includes amalgams of indium, gallium, thallium, bismuth, silver, gold, and zinc, along with an alloy of indium and gallium. The first metal can be selected from aluminum, magnesium, zinc, lead, silver, nickel and copper.

The selection of the second metal must be compatible with the properties of the first metal. For example, copper tends to absorb a considerable quantity of protons and thereby poisons a reaction unless a fast diffusing metal such as gallium is used. An equal part liquid mixture of indium and gallium appears to be most satisfactory in general for preparing an activated metal in accordance with the present invention.

An equal part of a liquid alloy of indium and gallium in contact with a highly pure aluminum rod in the presence of hydrochloric acid will bring about a dramatic change in the physical and chemically properties of the aluminum rod. The alloy can have a mass from 1 to 3% of the rod. The rod can have a mass of about 100 grams and a diameter of a half inch.

It should be understood that the term "highly pure" means greater than 99% and that purities in the order of 99.9% and 99.99% are desirable.

The proton source, which is not at all limited to hydrochloric acid has a pH of about 0.2–4 and completely covers the aluminum rod.

One striking indication that an activated metal has been formed is that the activated aluminum rod will cause a rapid disassociation of water as compared to an untreated rod. An untreated rod in water may show the formation of only small bubbles, particularly at a freshly cut end, whereas the activated rod in water will show bubbles over its entire surface.

Under high magnification, and activated metal in accordance with the present invention has been observed to have innumerable tiny channels which are believed to account in part for the unusually chemical activity.

An activated metal has a tendency to form a coating over its surface after exposure to air. The coating can build up considerably in time and should be removed before using the activated metal. The coating can be removed with hot water or boiling it in hot water or with an acid such as hydrochloric acid.

A freshly prepared activated metal prepared with a gallium and indium alloy can be briefly dipped into anhydrous methyl alcohol, say two or three minutes to avoid the formation of the coating.

Another example of preparing activated aluminum is to place 100 grams of a 99.9% pure aluminum rod having a half inch diameter in about two grams of mercury and cover the rod with hydrochloric acid having about 4pH. The vessel in this and other cases should be non-reactive material, such as glass. After most of the mercury has been absorbed a activated metal has been formed. More than two grams of mercury can be used but the reaction should be stopped when about two grams of mercury have been absorbed. Pouring cold water into the solution to dilute the acid greatly will virtually stop the reaction so that the rod can be removed. If the rod is removed to stop the reaction, overheating of the rod occurs and the channels tend to contract and squeeze the mercury out.

When an acid such as hydrochloric acid has been used in the preparation of an activated metal, it is desirable to purge the activated metal of residual hydrochloric acid so as not to disturb the subsequent formation of a metal salt. One way of prepared the activated metal is to run very hot water over the activated metal to thoroughly wash out the hydrochloric acid or other acid, depending upon what is used. In some cases, it may be convenient to use a carboxylic acid to form the activated metal particularly when the same carboxylic acid will be used subsequently. Because many of the carboxylic acids are weak acids, it may be necessary to heat the carboxylic acid when forming the activated metal. The added heat should not be sufficient to decompose the carboxylic acid. Naturally, if the same carboxylic acid is used to prepare the activated metal and to form the metal salt, the activated metal need not be washed at all.

Activated metals, other than aluminum can be used in the present invention to form metal salts. In this connection, several examples involving other activated metals will now be given. In particular, activated zinc, magnesium, nickel, or lead can be prepared by placing a rod of the appropriate metal, say about 100 grams, in a vessel with hydrochloric acid of about 4pH and contacting the metal with an equal part of the gallium and indium alloy having a mass of about two grams. The metal is preferably in the form of a rod having a diameter of about a half inch diameter. As with the activated aluminum, all activated metals should be washed in hot water to avoid contamination of the metal salt to be prepared from the hydrochloric acid.

SUMMARY OF THE INVENTION

The present invention makes use of unique properties of an activated metal by forming a metal salt of a carboxylic acid through the contacting of an activated metal with a carboxylic acid. The carboxylic acids which are water soluble lend themselves to the formation of a polymeric metal salt; the activated metal and carboxylic acid are contacted in the presence of an excess amount of water.

In the case of a water insoluble carboxylic acid, it has been found that a metal salt can be formed by positioning an acivated metal so that part of the activated metal is in water while another part of the activated metal contacts the carboxylic acid. The actual formation of the metal salt occurs in the vicinity of the boundary line of the water and the carboxylic acid at the activated metal. Applying heat to melt the carboxylic acid is preferred if the melting point of the carboxylic acid is less than 100°C and water is used.

A water insoluble carboxylic acid can also be reacted with an activated metal by combining the carboxylic acid, water, and the activated metal and agitating the mixture so that the carboxylic acid repeatedly contacts the activated metal.

Combining a water soluble carboxylic acid, an activated metal, and water where appropriate in a stoichiometric ratio as dictated by the formula of a desired metal salt will produce the desired metal salt. Metal salts of water insoluble carboxylic acids can be prepared similarly, in many cases for example, where the carboxylic acid can be liquified by heating.

THE INVENTION

In connection with the present invention it is noted that suitable carboxylic acids include percarboxylic acids, aliphatic carboxylic acids, aromatic mono and polybasic carboxylic acids. The pH of solutions in the practice of the invention are preferably less than about 4.2.

The carboxylic acids vary in physical properties which are relevant to the preparation of metal salts. For example, formic acid is a liquid at room temperature while stearic acid can be heated to a liquid at 69°C but para-benzene carboxylic sublimates. Another relevant property is solubility in water. In view of these varying physical properties, it has been found that the caboxylic acids should be handled somewhat differently in order to accommodate these physical properties. The water soluble carboxylic acid are most desirable since it is only necessary to dissolve the carboxylic acid in water and then insert the activated metal to form a metal salt. On the other hand, if the carboxylic acid is a liquid or can be made into a liquid by applying heat, one can just liquify the carboxylic acid and then insert the activated metal to form a metal salt, absent hydroxide bridges. The carboxylic acid which sublimates or, even worse, decomposes upon being heated must be handled in quite a different way. In these cases, a mixture of water, activated metal, and carboxylic acid can be combined in a vessel and agitated so that the metal salt forms on the activated metal as a result of the repeated contacting of the carboxylic acid and the acivated metal. Another way of handling the carboxylic acid which sublimates is to heat the carboxylic acid so that it turns to a vapor or gaseous form and have the gas contact the activated metal. It may be advantageous to conduct this last method in the presence of water vapor in order to continuously provide a hydrogen source to the activated metal.

In all methods of preparing a metal salt in accordance with the present invention it will always be advantageous to use either a freshly prepared activated metal or one freshly treated to be free of a surface coating. In the examples which follow a freshly treated activated metal is always intended.

The specific preparation of a polymeric metal salt is usually carried out by the combination of the activated metal, water soluble carboxylic acid, and an excess of water at room temperature or at a somewhat lower temperature.

In the examples which follow, it is to be understood that the invention is not to be limited to just these examples and variations within the scope and spirit of the disclosure herein will be apparent to persons skilled in the art.

EXAMPLE 1

To form a polymeric aluminum formate the formula $Al_2(OH)_5CHO_2.2H_2O$ is a good guide for the mass ratio of the activated and formic acid; an excess of water is added to assure the formation of the polymeric metal salt. About three times the amount of water predicated on the stoichiometry is satisfactory. The actual water of crystallization or even the formula can vary. The water of crystallization can easily range from one to three while the amount of aluminum need only be greater than about one atom per mol. Nevertheless, the formulas given herein provide a rational basis for apportioning the constituents. No limitation should be inferred from the presentation of model formulas for polymeric metal salts. Then, 51 grams of 90% formic acid, 54 grams of activated aluminum catalytic electrode, and 347 grams of water are combined in a beaker and left until the activated metal has been substantially consumed, which can take about two weeks at room temperature. Room temperature or somewhat cooler is preferred. During the reaction, hydrogen bubbles will be seen rising from the activated aluminum to the surface of the liquid. As polymerization progresses, the viscosity of the solution increases as evidenced by a slower rise of the bubbles, and the larger size of the bubbles needed to break free from the surface of the activated aluminum.

EXAMPLE 2

To form a polymeric aluminum oxalate the formula $Al_2(OH)_5C_2HO_4.22O$ is a satisfactory guide for the stoichrometry with, of course, an excess of water. Then 126 grams of oxalic acid, 54 grams of activated aluminum, and 432 grams of water are combined in the beaker and left until the activated aluminum has been substantially consumed. The reaction is run at room temperature in a manner similar to EXAMPLE 1.

EXAMPLE 3

A polymeric aluminum citrate can be made using the formula $Al_2(OH)_5C_6H_7.2H_2O$ as a guide, again with an excess of water. The constituents are 192 grams of citric acid (anhydrous), 54 grams of activated aluminum, and 499 grams of water. The reaction is run at room temperature until the activated aluminum has been substantially consumed.

EXAMPLE 4

A polymeric aluminum ascorbate is based on the stoichiometry in accordance with the formula $Al_2(OH)_5CH_2OHCHOHCHCOH=COCOO.2H_2O$. Excess water is used. The constituents are 176 grams of ascorbic acid, 54 grams of activated aluminum, and 483 grams of water. The reaction is run at room temperature until the activated aluminum has been substantially consumed.

EXAMPLE 5

A polymeric aluminum acetate is prepared based on the model formula $Al_2(OH)_5C_2H_3O_2.2H_2O$. The constituents including an excess of water are 60 grams of acetic acid, 54 grams of activated aluminum, and 366 grams of water. The reaction is run at room temperature until the activated aluminum has been substantially consumed.

Figure 1:
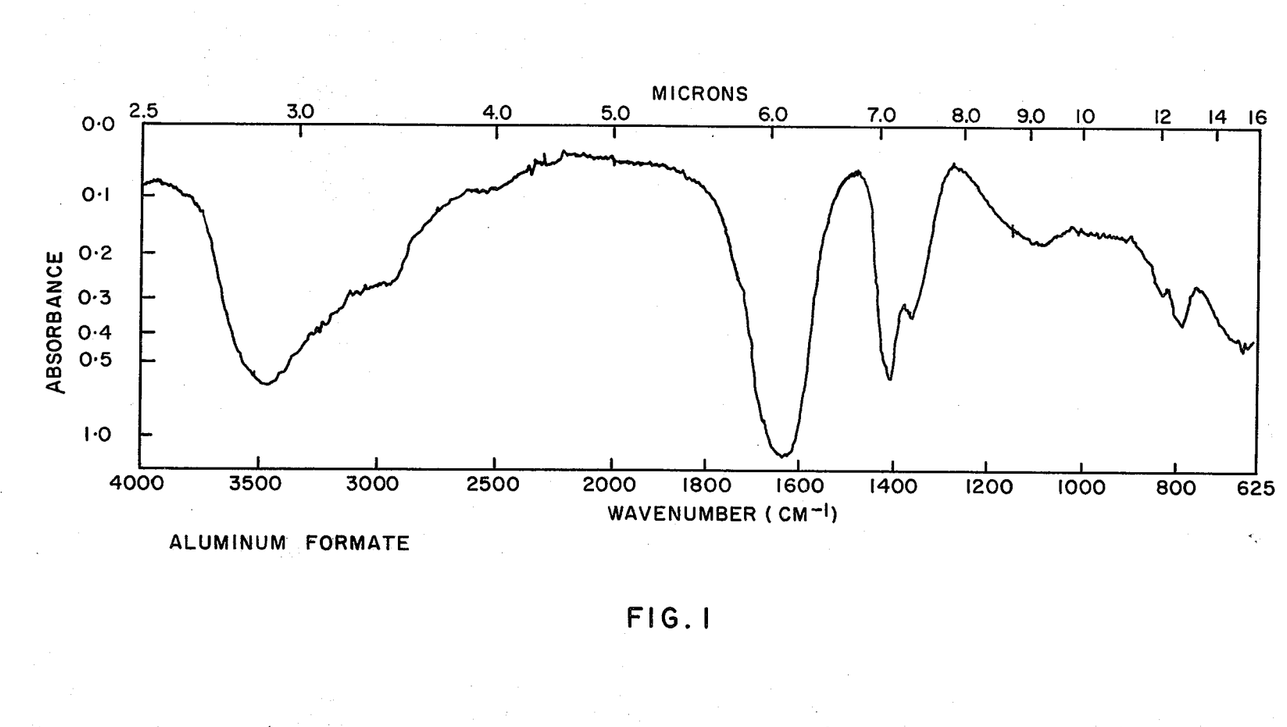
FIGS. 1–5 are infrared spectra responses corresponding to five polymeric metal salts of the present invention.
Figure 2:
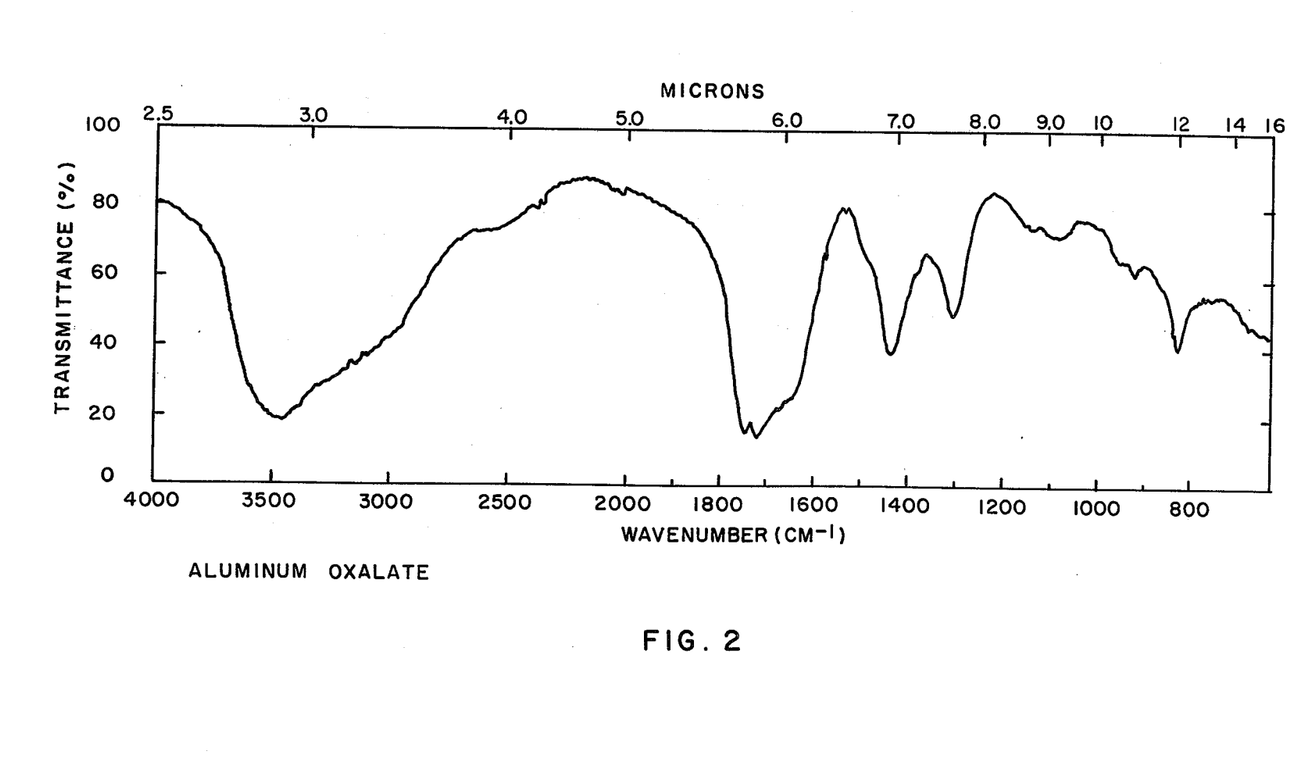
Figure 3:
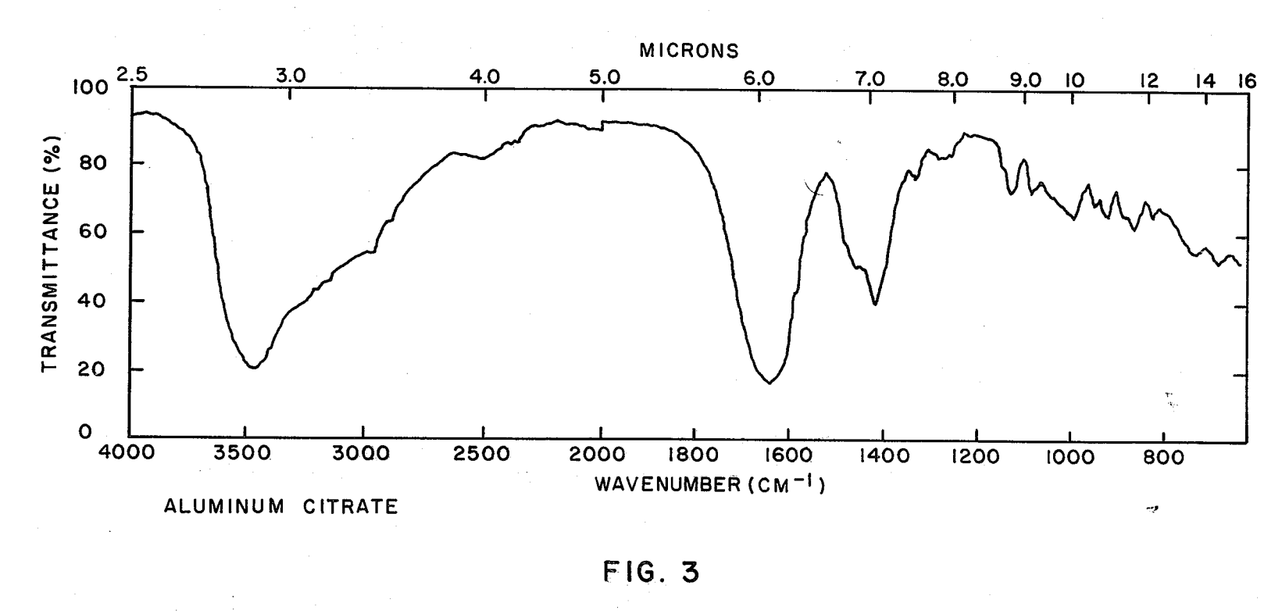
Figure 4:
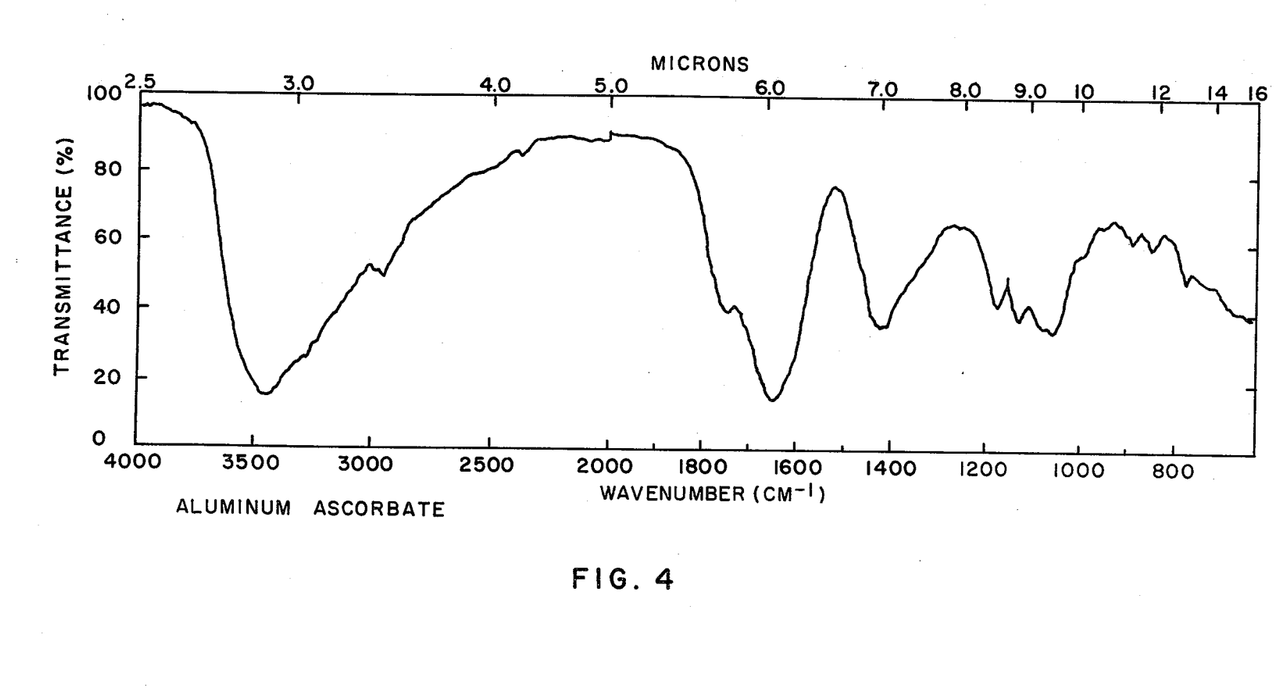
Figure 5:
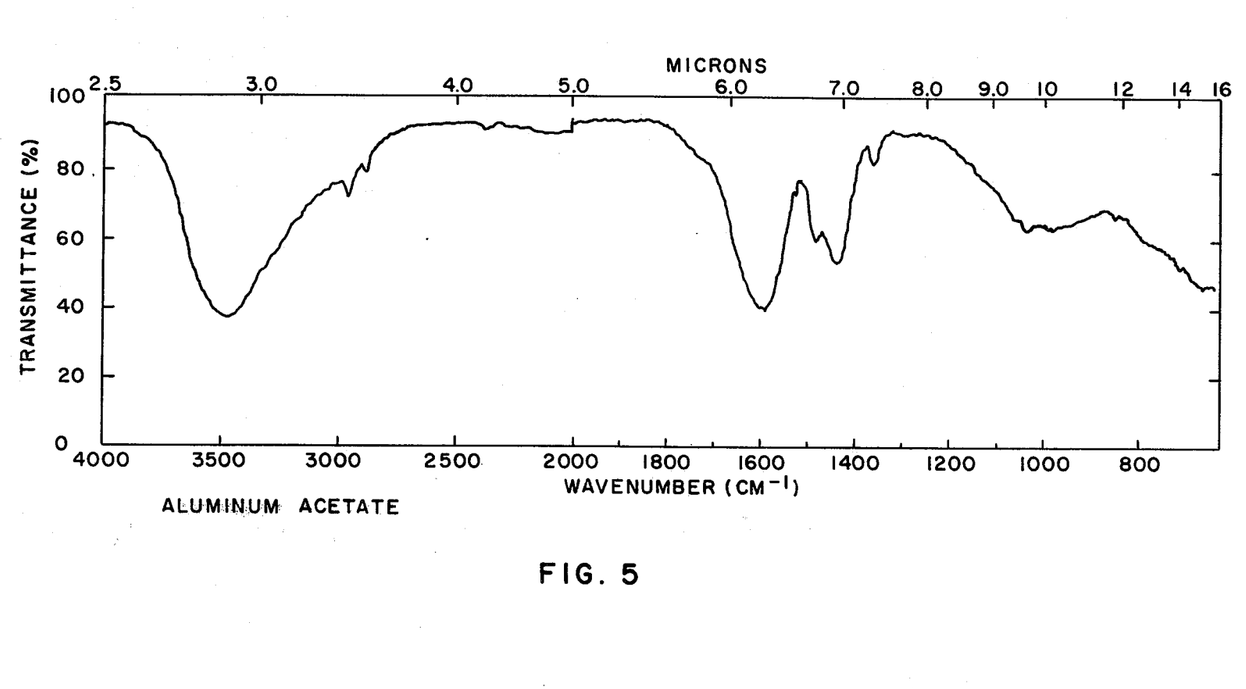

The polymers of EXAMPLES 1–5 are unique in many ways, including very high purity in addition to a novel structure. Figures FIGS. 1–5 show infrared spectra of the polymers of aluminum formate, aluminum oxalate, aluminum citrate, aluminum ascorbate, and aluminum acetate respectively. The infrared spectra graphs of FIGS. 1–5 are remarkably "clean"; that is, in the absence of numerous valleys and peaks resulting from the presence of impurities found in prior art formulations of polymeric metal salts.

Each sample for the infrared spectra measurement was prepared by well-known procedure of mixing about 1% by weight of the compound to be tested with potassium bromide and then forming a disc under a vacuum.

It universally is recognized that an infrared absorbtion spectrum of a compound, uniquely identifies the compound much like a fingerprint identifies an individual, in addition the infrared absorption spectra provides insight into the structure of the compound.

A glance at the figures indicates similarities between the variations such as valleys and flat regions. The flat regions or small shoulders in the figures generally correspond to minor absorption levels but have some significance when viewed with respect to corresponding shoulders or variations in other figures. Table 1 presents a correlation of variations which appear in the figures. In some cases a variation is a valley but the correlated variation in another figure is only a slight dip. Some further comment on Table 1 follows. The comments which follow are not intended to be a limitation but merely to be informative.

Variation number 1 corresponds to O-H stretching and the magnitude which appears in the drawings tends to verify the polymeric form of the compounds. Variation 2 is found in chelates and may be due to track ions or the like. It will be noticed that aluminum acetate shows two variations, Variation 3 corresponds to a region which is usually associated with a response to broad multiplex; no response appears evident for the ascorbate or the acetate. Variation 4 which appears in all the figures does not seem to relate to any well-known absorption response. On the other hand variations 5–8 are well-known to occur for metal salts. Some splitting or variation within a response region.

Some correlated variations present in the infrared spectra of FIGS. 1–5 occurs for the metal salts of higher carboxylic acids.

pound will produce an absorption depth about twice of either the absorption depths alone.

It should be understood that it is the gross variation of each of the figures which has significance and bearing to the respective polymeric compounds.

EXAMPLE 6

Polymeric aluminum formate can be made in a much shorter period of time by utilizing approximately six times the amount of activated aluminum; that is, about 324 grams of activated aluminum positioned at the bottom of the vessel as to permit the liquid to move passed the rods freely and letting the mixture stand for about twenty-four hours. After about twenty-four hours, a sample of the mixture should be checked to determine the ratio of the aluminum present. If the ratio is approximately 1.7 to 1 or as high as 1.9 to 1, then the mixture can be placed on a hot plate and heated for about ten minutes to finish the reaction. The reaction should be stopped for a titrated metal ratio of about 2 to 1. For that ratio, the liquid should be poured off immediately to prevent the activated aluminum from carrying the reaction further.

EXAMPLE 7

The procedure described in EXAMPLE 6 can be

TABLE I

| Variation Number | Aluminum formate $CM^{-1}$ | Aluminum oxalate $CM^{-1}$ | Aluminum citrate $CM^{-1}$ | Aluminum ascorbate $CM^{-1}$ | Aluminum acetate $CM^{-1}$ |
|---|---|---|---|---|---|
| 1. | 3460 | 3460 | 3460 | 3445 | 3465 |
| 2. | 2940 | 2940 | 2960 | 2960 | 2960 2880 |
| 3. | 2540 | 2540 | 2500 | — | — |
| 4. | 2350 | 2370 1745 | 2380 | 2380 1750 | 2380 1765 |
| 5. | 1640 | 1720 | 1640 1455 | 1645 | 1590 1485 |
| 6. | 1420 | 1440 | 1415 1330 | 1420 | 1440 |
| 7. | 1320 | 1310 | 1270 | — 1170 1130 | 1360 |
| 8. | 1165 | 1185 1140 | 1125 | 1080 1055 | 1140 1035 |
| 9. | 830 | 830 | 990 940 920 860 820 | 990 950 890 850 | 930 850 |
| 10. | 790 | 760 | 730 | 770 | 760 |
| 11. | 660 | 660 | 680 | 670 | 660 | occurs for the metal salts of higher carboxylic acids. Variation 9 may be due to free oxygen trapped within the chelate structure of the polymers. Variatons 10 and 11 occur within regions known to show absorption for organometallic compounds. Due to the novelty of organoaluminum compounds not very much data is available.

The depth of the valley in the region of 1650 to 1750 cm$^{-1}$ has particularly important significance in that the valley in this region substantiates the proposed polymeric structure as set forth above. It is known that the organic acid will show H bonds in this region, as well as aluminum to hydrogen bonding. As a matter of fact, it has been noted in the prior art that an organic acid will show about a medium absorption depth in this region as well as a compound having only aluminum to hydrogen bond. Polymeric compounds of the type shown in the figures bear out the expectation that the combination of hydrogen bonding in the organic part of the compound and the hydrogen bonding in the inorganic comfollowed for EXAMPLE 2 in order to obtain a polymeric metal salt of aluminum oxalate in a shorter time.

EXAMPLE 8

The procedure in EXAMPLE 6 can be applied for the case of EXAMPLE 3 in order to produce a polymeric aluminum citrate in a shorter time.

EXAMPLE 9

The procedure of EXAMPLE 6 can be applied to the preparation of the polymeric aluminum ascorbate in EXAMPLE 4 in order to shorten the preparation time.

EXAMPLE 10

The procedure of EXAMPLE 6 can be applied to the preparation of polymeric aluminum acetate described in EXAMPLE 5 in order to shorten preparation time.

It is convenient to pour off the polymeric metal salts of EXAMPLES 1 to 10 and permit them to gel or solidify. The time for solidification depends upon the amount of excess water. If it is found that the amount of water in the reaction results in a very long time for gelling, it may be desirable to use somewhat less water in the reaction. Too little water tends to permit the formation of ordinary metal salts. Both the polymeric metal salt solution and solid are water clear.

Other examples for preparing polymeric metal salts follow.

EXAMPLE 11

The preparation of a polymeric aluminum maleic follows the preparation procedure of EXAMPLE 1 and is based on the formula $Al_2(OH)_5CO_2HCH:CHCO_2$. Specifically 116 grams of maleic acid; 54 grams of activated aluminum, and 423 grams of water are combined in a vessel and left to react at room temperature until the activated aluminum has been substantially consumed.

EXAMPLE 12

The preparation of polymeric aluminum gluconate is similar to the preparation procedure of EXAMPLE 11, with the model formula being $Al_2(OH)_5CH_2OH(CHOH)_3CO_2.2H_2O$. The constituents are 392 grams of a 50% solution of gluconic acid, 54 grams of activated aluminum and 307 grams of water. The mixture is left at room temperature until the activated aluminum has been substantially consumed.

EXAMPLE 13

A polymeric aluminum lactate is prepared in a similar manner to that described in EXAMPLE 11 with the constituents following the formula $Al_2(OH)_5CH_3CHOHCO_2.2H_2O$. A typical batch comprises 106 grams of a 85% solution of lactic acid; 54 grams of activated aluminum and 381 grams of water. The mixture is left at room temperature until the activated aluminum has been substantially consumed.

EXAMPLE 14

A polymeric aluminum butyrate is prepared in a similar manner to EXAMPLE 11, using the model formula $Al_2(OH)_5(CH_3)_2CO_2.2H_2O$. A typical batch includes 88 grams of buteric acid; 54 grams of activated aluminum, and 395 grams of water. The batches are left at room temperature until the activated aluminum has been consumed.

EXAMPLE 15

The preparation of polymeric aluminum benzoate follows the model formula $Al_2(OH)_5C_6H_5CO_2.2H_2O$. A typical batch includes 122 grams of benzoate acid, 54 grams of freshly activated aluminum and 429 grams of water. The mixture is left at room temperature until the activated aluminum has been substantially consumed.

EXAMPLE 16

The preparation of a polymeric aluminum palmitate follows EXAMPLE 11 but uses the model formula $Al_2(OH)_5(CH_2)_{14}CO_2.2H_2O$. A typical batch includes 256 grams of palmitic acid, 54 grams of activated aluminum, and 562 grams of water. The mixture is left at room temperature until the activated aluminum has been substantially consumed.

EXAMPLE 17

A polymeric aluminum oleate follows EXAMPLE 11, but uses the model formula $Al_2(OH)_5C_{18}H_{33}O_2.2H_2O$. The typical batch is 282 grams of oleic acid, 54 grams of activated aluminum and 589 grams of water. The batch is left at room temperature until the activated aluminum has been substantially consumed.

EXAMPLE 18

A polymeric aluminum myristate follows EXAMPLE 11, but uses the model formula $Al_2(OH)_5CH_3(CH_2)_{12}CO_2.2H_2O$. A typical batch is 228 grams of myristic acid, 54 grams of activated aluminum, and 535 grams of water. The batch is left at room temperature until the activated aluminum has been substantially consumed.

EXAMPLE 19

A polymeric aluminum acrylate follows the model formula $Al_2(OH)_5CH_2:CH.CO_2.2H_2O$ with a typical batch including 72 grams of acrylic acid, 54 grams of activated aluminum, and 300 grams of water. The batch is left at room temperature until the activated aluminum has been substantially consumed.

EXAMPLE 20

A polymeric aluminum vinyl acetate follows the model formula $Al_2CH_2:CHCH_2CO_2.2H_2O$ with a typical batch being 86 grams of vinyl acetic acid, 54 grams of activated aluminum and 300 grams of water. The batch is left at room temperature until the activated aluminum has been substantially consumed.

From the aforementioned specific examples of polymeric metal salts, it is clear that the preparation of a polymeric metal salt utilizes a quantity of water well beyond the amount indicated by the model formulas.

The following forms a general guide but not a limitation for the preparation of a polymeric metal salt:

For a water soluble carboxylic acid and ignoring any possible complications, arising from a polyprotic acid, the general model formula is $A_2(OH)_{2a-1}R.XH_2O$ where A is a metal having a valence of a and R is the hydrocarbon. The value of X can range from unity to three. Naturally, any question of the value of X should favor the greater value if the amount of water for the reaction is to be determined. This formula cannot precisely describe the complex polymeric metal salt which may link to form even a higher ratio of metal to hydrocarbon. On the other hand, a lower ratio of metal to hydrocarbon may be found desirable for come applications, such as in a detergent.

The preparation of a polymeric metal salt at room temperature in accordance with the suggested model formula should result in a water clear liquid which will usually gel to a water clear solid. It may be necessary to wait until some of the water has evaporated. Some mild heat can be used to promote the evaporation but too high a temperature, such as boiling may drive off the extra water and then start to break up to polymeric metal salt. Of course, if it is found that too much water is in the product, less water can be used to start. In some cases, the cost of driving off extra water is conveniently avoided by starting with less water.

One general measure of constituents to form a polymeric metal salt based on the general model formula is two mols of the activated metal, one mol of a water soluble carboxylic acid, and $3(2a+1)$ mols of water where "a" is the valence of the metal. If less than two to one ratio of metal to hydrocarbon is desired, either the reaction can be monitored by titration and stopped at the desired ratio or less of the activated metal can be used at the start.

Other examples for preparing polymeric metal salt follow.

EXAMPLE 21

A polymeric nickel acetate uses the model formula $Ni_2(OH)_3(C_2H_3O_2).2H_2O$ and the constituents are 60 grams of acetic acid, 117 grams of activated nickel, and 601 grams of water. The mixture is left at room temperature until the activated nickel has been substantially consumed.

EXAMPLE 22

A polymeric lead acetate is guided by the model formula $Pb(OH)_3(C_2H_3O_2).2H_2O$ and EXAMPLE 19 and uses 60 grams of acetic acid, 414 grams of activated lead, and 843 grams of water.

EXAMPLE 23

A polymeric magnesium acetate uses the model formula $Mg(OH)_3(C_2H_3O_2).2H_2O$ to combine 60 grams of acetic acid, 48 grams of activated magnesium, and 294 grams of water at room temperature. Again, the mixture is left until the activated magnesium has been substantially consumed.

Polymeric magnesium salts, especially of oil soluble carboxylic acids, are widely used as additives for fuels and lubricants. Of the prior art methods of preparation, the method of U.S. Pat. No. 3,629,109 is probably the easiest. The patent teaches the use of commercial active magnesium oxide for over basing to produce a complex product which includes the polymeric magnesium salt. The method of the patent calls for a promoter of water or of water and alcohol. The use of water alone tends to cause the solution to become cloudy, thereby indicating the presence of something other than a pure polymeric magnesium salt. The water and alcohol combination avoids the clouding but the product lacks purity.

EXAMPLE 24

A polymeric zinc acetate uses 60 grams of acetic acid, 131 grams of activated zinc, and 250 grams of water. The mixture is left at room temperature until the activated zinc has been substantially consumed.

Turning now to the preparation of ordinary stoichiometric metal salts of carboxylic acids, it happens that even metal salts predicted by the valence rules but beyond prior art methods are easily prepared. A feature of these metal salts, as with the polymeric metal salts, is the absence of impurities. Or, to put it more positively, the metal salts of the invention have very high purity. The stoichimetry of the respective formulas are followed.

EXAMPLE 25

To prepare aluminum monoacetate, $Al(OH)_2(C_2H_3O_2)$, combine 60 grams of acetic acid, 27 grams of activated aluminum and 34 grams of water. The mixture should be left at room temperature until the activated metal has been substantially consumed.

EXAMPLE 26

To prepare aluminum diacetate, $Al(OH)(C_2H_3O_2)_2$, combine 120 grams of acetic acid, 27 grams of activated aluminum, and 18 grams of water at room temperature. The mixture should be left until the activated aluminum has been substantially consumed.

EXAMPLE 27

To prepare aluminum triacetate, $Al(C_2H_3O_2)_3$, combine 180 grams of acetic acid, and 27 grams of activated aluminum at room temperature. The mixture should be left until the catalytic electrode has been substantially consumed.

EXAMPLE 28

To prepare aluminum diformate, $Al(OH)(CHO_2)_2$, combine 94 grams of formic acid, 18 grams of water, and 27 grams of activated aluminum. The mixture is left at room temperature until the activated aluminum has been substantially consumed.

EXAMPLE 29

To prepare aluminum triformate, $Al(CHO_2)_3.3H_2O$, combine 144 of formic acid, 27 grams of activated aluminum and 54 grams of water. The mixture is left at room temperature until the activated aluminum has been substantially consumed.

EXAMPLE 30

To prepare aluminum palmitate $Al(OH)_2(C_{16}H_{31}O_2)$, combine 769 grams of palmitic acid, 36 grams of water and 27 grams of activated aluminum. The mixture is left at room temperature until the activated aluminum has been substantially consumed.

The products of EXAMPLES 25 to 30 are white powders whereas the prior art methods result in a white to yellow powder. The variation in color found in the prior art aluminum palmitate suggests the presence of impurities while the product of the present method has extremely high purity.

EXAMPLE 31

To prepare aluminum oleate, $Al(C_{18}H_{33}O_2)_3$, combine 847 grams of oleic acid and 27 grams of freshly activated aluminum. The mixture is left at room temperature until the activated aluminum has been substantially consumed.

The aluminum oleate of EXAMPLE 31 is a white powder in contrast to the yellowish mass which results from prior art preparations. The difference in the colors and physical properties are probably due to the very high purity of the product produced by the present methods.

EXAMPLE 32

To prepare aluminum oxalate, $Al(C_2HO_2)_3.4H_2O$, combine 384 grams of oxalic acid, 72 grams of water, and 27 grams of activated aluminum. The mixture is left at room temperature until the activated aluminum has been substantially consumed.

EXAMPLE 33

To prepare aluminum lactate, $Al(C_3H_5O_3)_3$, combine 270 grams of lactic acid and 27 grams of activated aluminum at room temperature. The product is a fine white powder in contrast to the prior art product which is a yellowish white powder.

EXAMPLE 34

To prepare aluminum benzoate, $Al(C_7H_5O_2)_3$, combine 366 grams of benzoic acid and 27 grams of activated aluminum at room temperature. The mixture should be left until the activated aluminum has been substantially consumed.

EXAMPLE 35

To prepare aluminum stearate, $Al(C_{18}H_{35}O_2)_3$, combine 27 grams of activated aluminum and 847 grams of stearic acid and supply sufficient heat to liquify the stearic acid. The reaction should be continued until the activated aluminum has been consumed.

EXAMPLE 36

To prepare nickel acetate, $Ni(C_2H_3O_2)_2$, combine 59 grams of activated nickel and 118 grams of acetic acid and proceed as in EXAMPLE 26.

EXAMPLE 37

To prepare nickel stearate, $Ni(C_{18}H_{35}O_2)_2$, combine 58 grams of activated nickel and 567 grams of stearic acid and add sufficient heat to liquify the stearic acid. The activated nickel should be substantially consumed.

EXAMPLE 38

To prepare lead acetate, $Pb(C_2H_3O_2)_2$, combine 207 grams of activated lead and 118 grams of acetic acid and proceed as in EXAMPLE 26.

EXAMPLE 39

To prepare lead triacetate, $Pb_2(OH)(C_2H_3O_2)_3$, combine 414 grams of activated lead and 180 grams of acetic acid and proceed as in EXAMPLE 26.

EXAMPLE 40

To prepare lead acetate, $Pb(C_2H_3O_2)_4$, combine 207 grams of activated lead and 236 grams of acetic acid. The mixture should be permitted to react at a temperature below 20°C in order to accommodate the combination with the valence of four for the lead rather than a valence of two.

EXAMPLE 41

To prepare magnesium acetate, $Mg(C_2H_3O_2)_2$, combine 24 grams of activated magnesium and 118 grams of acetic acid and proceed as in EXAMPLE 26.

EXAMPLE 42

To prepare zinc acetate, $Zn(C_2H_3O_2)_2$, combine 65 grams of activated zinc and 118 grams of acetic acid and proceed as in EXAMPLE 26.

EXAMPLE 43

To prepare zinc stearate, $Zn(C_{18}H_{35}O_2)_2$, combine 65 grams of activated zinc and 567 grams of stearic acid and add sufficient heat to liquify the stearic acid. The reaction should continue until the activated zinc has been substantially consumed.

EXAMPLE 44

Another way to prepare aluminum stearate is by placing activated aluminum in a glass vessel and adding sufficient water to cover about half the activated aluminum and then adding a small quantity of stearic acid. The activated aluminum will react with the water and with the stearic acid at the surface where the water meets the activated aluminum. Aluminum stearate is formed at room temperature.

EXAMPLE 45

EXAMPLE 44 can be repeated with the addition of sufficient heat to liquify the stearic acid.

EXAMPLE 46

Yet another way to prepare aluminum stearate is to combine activated aluminum, water and stearic acid and agitate the mixture to contact the activated aluminum and the stearic acid repeatedly and maintain a movement of water about the surface of the activated aluminum. This procedure is also suitable for carboxylic acids which are insoluble in water.

EXAMPLE 47

To prepare an aluminum salt of para-benzene dicarboxylic acid (terephthalic), $C_6H_4(COOH)_2(1,4)$, consideration must be given to the fact that the acid sublimates. Heat 20 grams of the acid so that the vapors rise and contact water wet activated aluminum above the acid. THe activated aluminum is about 54 grams and in the shape of a rod with a diameter of a half inch. The compound formed at the surface of the activated aluminum will be the aluminum salt.

EXAMPLE 48

The aluminum salt of EXAMPLE 47 can also be produced by maintaining water vapor in the vicinity of the activated aluminum in order to promote the formation of hydrogen and thereby stimulate the combination to form the metal salt.

EXAMPLE 49

The aluminum salt of EXAMPLE 47 can be produced by proceeding as in EXAMPLE 47 with the additional step of running water on the activated aluminum.

I claim:
1. A method of preparing a metal-carboxylic acid compound which comprises:
   reacting, by contacting:
   a. an activated metal comprising (i) a high purity first metal selected from group consisting of aluminum, zinc, magnesium, lead, nickel, silver and copper, permeated with (ii) a second metal selected from mercury, indium, gallium and alloys of indium and gallium; and
   b. a carboxylic acid, whereby said first metal is consumed in reaction with said carboxylic acid, thereby forming said metal-carboxylic acid compound.
2. The method of claim 1, wherein said carboxylic acid is soluble in water and the reaction of said activated metal and carboxylic acid is conducted in an aqueous medium.
3. The method of claim 2, wherein the aqueous medium is present in a stoichiometric excess based on the water of crystallization of said metal-carboxylic acid compound.
4. The method of claim 3, wherein the valence of said first metal is "a" and the quantity of water of said aqueous medium is at least $3(2a+1)$ times the number of moles of said carboxylic acid.
5. The method of claim 1, wherein said carboxylic acid is insoluble in water and the reaction of said activated metal and carboxylic acid is conducted in an aqueous medium with agitation sufficient to provide contact between said carboxylic acid and activated metal.
6. The method of claim 1, wherein the reaction is carried out at a pH of less then about 4.2.

7. The method of claim 1, wherein said second metal is mercury.

8. The method of claim 1, wherein said second metal is an alloy of indium and gallium.

9. The method of claim 1, wherein said first metal has a purity of at least 99.99% by weight.

* * * * *